(12) United States Patent
Schlienger et al.

(10) Patent No.: US 9,237,909 B2
(45) Date of Patent: Jan. 19, 2016

(54) SURGICAL NAIL

(75) Inventors: André Schlienger, Arlesheim (CH);
Dankward Höntzsch, Tübingen (DE);
Markus Buettler, Mümliswil (CH);
Peter Senn, Waldenburg (CH)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 2563 days.

(21) Appl. No.: 11/343,857

(22) Filed: Jan. 30, 2006

(65) Prior Publication Data

US 2006/0189988 A1   Aug. 24, 2006

Related U.S. Application Data

(63) Continuation of application No. PCT/CH03/00519, filed on Jul. 30, 2003.

(51) Int. Cl.
*A61B 17/72* (2006.01)
*A61B 17/00* (2006.01)

(52) U.S. Cl.
CPC .............. *A61B 17/72* (2013.01); *A61B 17/7233* (2013.01); *A61B 2017/00004* (2013.01)

(58) Field of Classification Search
CPC ....................................... A61B 17/72–17/7291
USPC ....................... 606/62–68, 98, 329; 623/23.23
See application file for complete search history.

(56) References Cited

U.S. PATENT DOCUMENTS

| | | |
|---|---|---|
| 2,834,342 A | 5/1958 | Yost |
| 3,255,747 A | 6/1966 | Cochran et al. |
| 3,433,220 A | 3/1969 | Zickel |
| 4,095,591 A | 6/1978 | Graham, Jr. et al. |
| 4,103,683 A | 8/1978 | Neufeld |

(Continued)

FOREIGN PATENT DOCUMENTS

| | | |
|---|---|---|
| CH | 668 173 | 12/1988 |
| CH | 674 613 | 6/1990 |

(Continued)

OTHER PUBLICATIONS

International Search Report for International Application No. PCT/CH03/00519, mailed Mar. 25, 2004, German language version.

(Continued)

*Primary Examiner* — Jan Christopher Merene
*Assistant Examiner* — Steven Cotroneo
(74) *Attorney, Agent, or Firm* — Fay Kaplun & Marcin, LLP

(57) ABSTRACT

The surgical nail, here in the form of an intramedullary nail, has a central axis, a longitudinal borehole with a diameter D extending coaxially with the central axis, a casing with an inner surface and a transverse borehole, extending transversely to the central axis with the cross-sectional profile F and the borehole axis. A component, which narrows the cross-sectional profile F, is provided in the longitudinal borehole in the region of the transverse borehole. By these means, the clearance, which is usually present between the medullary nail and the locking screws that have been introduced therein, can be eliminated without risk and an improved holding force as well as an improved guiding effect between the locking screw and the medullary nail can be achieved.

17 Claims, 2 Drawing Sheets

(56) References Cited

U.S. PATENT DOCUMENTS

| | | |
|---|---|---|
| 4,172,452 A | 10/1979 | Forte et al. |
| 4,274,163 A | 6/1981 | Malcom et al. |
| 4,438,762 A | 3/1984 | Kyle |
| 4,494,535 A | 1/1985 | Haig |
| 4,612,920 A | 9/1986 | Lower |
| 4,621,628 A | 11/1986 | Brudermann |
| 4,622,959 A | 11/1986 | Marcus |
| 4,657,001 A | 4/1987 | Fixel |
| 4,697,585 A | 10/1987 | Williams |
| 4,705,027 A | 11/1987 | Klaue |
| 4,754,749 A | 7/1988 | Tsou |
| 4,776,330 A | 10/1988 | Chapman et al. |
| 4,791,918 A | 12/1988 | Von Hasselbach |
| 4,817,591 A | 4/1989 | Klaue |
| 4,973,332 A | 11/1990 | Kummer |
| 5,032,125 A | 7/1991 | Durham et al. |
| 5,034,012 A * | 7/1991 | Frigg ............ 606/62 |
| 5,041,114 A | 8/1991 | Chapman et al. |
| 5,041,115 A | 8/1991 | Frigg et al. |
| 5,120,171 A | 6/1992 | Lasner |
| 5,167,663 A | 12/1992 | Brumfield |
| 5,176,681 A | 1/1993 | Lawes et al. |
| 5,300,074 A | 4/1994 | Frigg |
| 5,312,406 A | 5/1994 | Brumfield |
| 5,364,398 A | 11/1994 | Chapman et al. |
| 5,454,813 A | 10/1995 | Lawes |
| 5,484,439 A | 1/1996 | Olson et al. |
| 5,549,610 A | 8/1996 | Russell et al. |
| 5,573,536 A | 11/1996 | Grosse et al. |
| 5,578,035 A | 11/1996 | Lin |
| 5,591,168 A | 1/1997 | Judet et al. |
| 5,658,287 A | 8/1997 | Hofmann et al. |
| 5,658,339 A | 8/1997 | Tronzo et al. |
| 5,713,901 A | 2/1998 | Tock |
| 5,713,902 A | 2/1998 | Friedl |
| 5,728,099 A | 3/1998 | Tellman et al. |
| 5,741,256 A | 4/1998 | Bresina |
| 5,772,662 A | 6/1998 | Chapman et al. |
| 5,908,422 A | 6/1999 | Bresina |
| 5,928,235 A | 7/1999 | Friedl |
| 5,935,127 A | 8/1999 | Border |
| 5,976,139 A | 11/1999 | Bramlet |
| 6,010,506 A | 1/2000 | Gosney et al. |
| 6,059,785 A | 5/2000 | Schavan et al. |
| 6,123,708 A | 9/2000 | Kilpela et al. |
| 6,126,661 A | 10/2000 | Faccioli et al. |
| 6,187,007 B1 | 2/2001 | Frigg et al. |
| 6,228,086 B1 * | 5/2001 | Wahl et al. ............ 606/67 |
| 6,231,576 B1 * | 5/2001 | Frigg et al. ............ 606/62 |
| 6,235,031 B1 * | 5/2001 | Hodgeman et al. ............ 606/64 |
| 6,296,645 B1 | 10/2001 | Hover et al. |
| 6,454,810 B1 | 9/2002 | Lob |
| 6,783,529 B2 * | 8/2004 | Hover et al. ............ 606/62 |
| 7,182,765 B2 | 2/2007 | Roth et al. |
| 2002/0151898 A1 | 10/2002 | Sohngen et al. |
| 2002/0173792 A1 * | 11/2002 | Severns et al. ............ 606/62 |
| 2003/0069581 A1 | 4/2003 | Stinson et al. |
| 2003/0074000 A1 * | 4/2003 | Roth et al. ............ 606/62 |
| 2003/0114855 A1 | 6/2003 | Wahl et al. |
| 2006/0064095 A1 | 3/2006 | Senn et al. |
| 2006/0111716 A1 | 5/2006 | Schlienger et al. |
| 2006/0149248 A1 | 7/2006 | Schlienger et al. |
| 2006/0161155 A1 | 7/2006 | Schlienger et al. |
| 2006/0235395 A1 | 10/2006 | Frigg et al. |
| 2006/0241605 A1 | 10/2006 | Schlienger et al. |

FOREIGN PATENT DOCUMENTS

| | | |
|---|---|---|
| DE | 196 29 011 A1 | 1/1998 |
| DE | 199 45 611 A1 | 9/2001 |
| EP | 0 251 583 A2 | 1/1988 |
| EP | 0 321 170 B1 | 6/1989 |
| EP | 0 381 462 A2 | 8/1990 |
| EP | 0 411 273 A1 | 2/1991 |
| EP | 0 471 418 A1 | 2/1992 |
| EP | 0 838 199 A1 | 4/1998 |
| EP | 0 845 245 A2 | 6/1998 |
| EP | 0 853 923 A1 | 7/1998 |
| EP | 0 919 200 A1 | 6/1999 |
| EP | 0 968 685 A2 | 6/1999 |
| EP | 1 053 718 A1 | 11/2000 |
| EP | 1 214 914 A2 | 6/2002 |
| EP | 1 260 188 A1 | 11/2002 |
| FR | 2 784 283 | 4/2000 |
| GB | 2209947 A | 6/1989 |
| JP | 09-066059 | 3/1997 |
| JP | 09-066060 | 3/1997 |
| JP | 09-066061 | 3/1997 |
| JP | 11-137566 | 5/1999 |
| JP | 2000-051224 | 2/2000 |
| JP | 2000-051225 | 2/2000 |
| JP | 2000-342596 | 12/2000 |
| WO | WO 93/15679 | 8/1993 |
| WO | WO 96/15737 | 5/1996 |
| WO | WO 97/37606 | 10/1997 |
| WO | WO 98/05263 | 2/1998 |
| WO | WO 98/30164 | 7/1998 |
| WO | WO 98/41161 | 9/1998 |
| WO | WO 98/46169 | 10/1998 |
| WO | WO 00/67653 | 11/2000 |
| WO | WO 02/060331 | 8/2002 |
| WO | WO 03/015649 | 2/2003 |

OTHER PUBLICATIONS

International Search Report for International Application No. PCT/CH03/00519, mailed Mar. 25, 2004, English language translation of the German language version.

International Preliminary Examination Report for International Application No. PCT/CH03/00519, completed Jan. 17, 2006, German language version.

International Preliminary Examination Report for International Application No. PCT/CH03/00519, completed Jan. 17, 2006. English language translation of the German language version.

\* cited by examiner

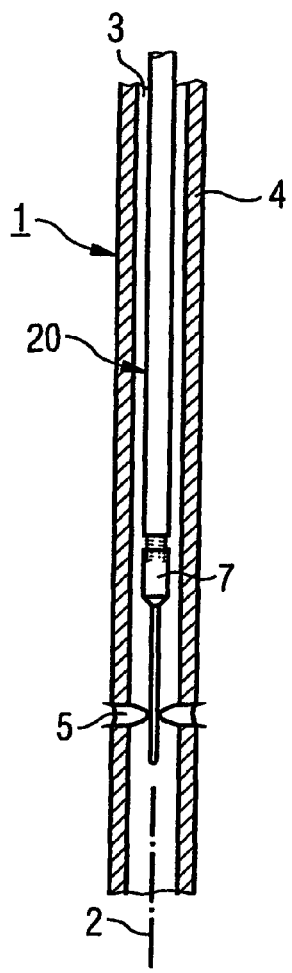
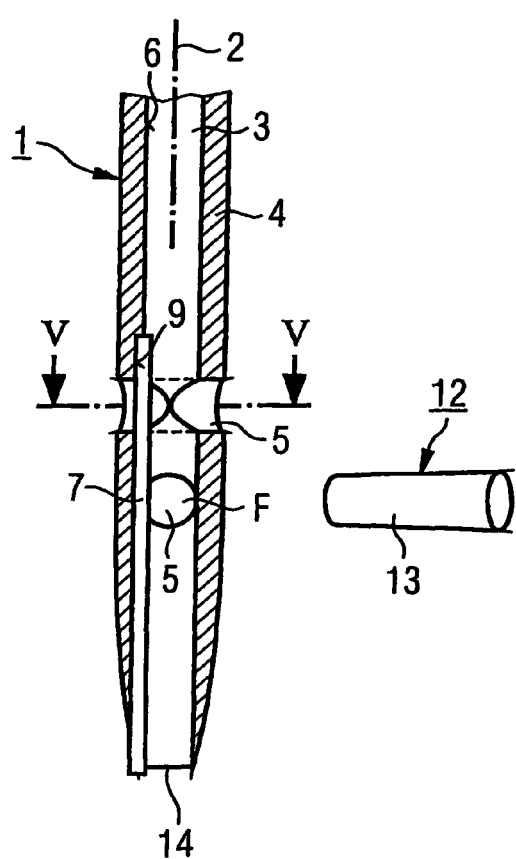
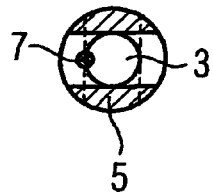

SURGICAL NAIL

RELATED APPLICATION DATA

The present application is a continuation of the U.S. National Stage designation of co-pending International Patent Application No. PCT/CH2003/000519 filed Jul. 30, 2003, the entire content of which is expressly incorporated herein by reference thereto.

FIELD OF THE INVENTION

The invention relates to a surgical nail, especially an intramedullary nail.

BACKGROUND OF THE INVENTION

The locking of intramedullary nails is known in the art. The introduction of locking screws or locking bolts (hereinafter referred to collectively as "locking screws") into the transverse bores of a intramedullary nail is carried out either with the aid of an imaging process (X-ray control) or a relatively complicated aiming device. In both cases, a certain aiming inaccuracy is unavoidable because the tip of the screw cannot be aligned exactly coaxially with the central axis of the transverse bore, and instead deviates therefrom by a certain amount. In order to enable the locking screw to enter into and pass through the transverse bore despite this aiming error, the outside diameter of the screw is underdimensioned such that it will be less than the diameter of the transverse bore. If the aiming accuracy remains within the range of this underdimensioning, the locking screw can be guided, despite the aiming error, through the transverse bore without any problem. In any case, as a result of the underdimensioning, the locking screw has a certain play or clearance relative to the transverse bore.

This clearance defines the amount by which the main bone fragments, which are fixed by means of locking screws in the corresponding locking hole, can move relative to the nail, and, because of the rigidity of the nail, move relative to the other main bone fragments fastened with the same nail. While some play or clearance is essential to guarantee the usefulness of the locking for surgeons, in the case of some indications (e.g. in the case of metaphysical fragments) it is clinically undesirable.

Even nails with a full cross section, which may have an internal thread in the locking hole, are not without clearance. The internal thread merely prevents axial movement of the nail on the locking screw.

U.S. Pat. No. 6,296,645 to HOVER et al. discloses a hollow, metallic intramedullary nail with diametrically opposed openings on the jacket of the transverse bore, described as windows, having one or two plastic inserts through which the locking screw can be introduced. A disadvantage of this known intramedullary nail is that the window-like plastic inserts can be easily pushed in, such that their desired function is lost. Even with a careful manipulation, the two plastic inserts can be pushed out from their "windows," which also leads to a loss of function.

SUMMARY OF THE INVENTION

The present invention seeks to remedy this problem. It is, therefore, an object of the invention to provide a surgical nail, especially an intramedullary nail, where the clearance between the nail and the locking screw can be eliminated without risk, and where an improved holding force as well as an improved guiding effect can be achieved between the locking screw and the medullary nail.

Pursuant to a preferred embodiment of the invention, this objective is accomplished with a surgical nail comprising a nail body having a central longitudinal axis, an outer wall surrounding a longitudinal bore and defining an inner wall surface, and a transverse opening through the outer wall. The transverse opening has a central axis and a cross-sectional profile F and is configured for receiving a bone fixation element, e.g., bone screw, bolt, etc. A longitudinal component, e.g., pin, stud, cable, wire, etc., is disposed within the longitudinal bore near the transverse opening, and the longitudinal component is configured and dimensioned for narrowing the cross-sectional profile F while still permitting passage of the bone fixation element through the transverse opening.

With that, the following advantages can be achieved:

the targeting accuracy is not affected during the introduction of the locking screw;

the possibility exists of fixing the bone fragments angularly stably in certain directions for a particular amount of the load;

after the corticalis is drilled, the component can be brought into the medullary nail, that is, exogenous chips are not formed in the medullary canal and a greater or lesser angular stability of the locking screw can be achieved depending on the components selected.

In the case of a particular embodiment, the component consists of a stud, a piece of wire or a piece of cable, which is aligned essentially parallel to the longitudinal axis of the nail.

In the case of a preferred embodiment, the component consists of the same material as the medullary nail, that is, of titanium or a titanium alloy for a titanium nail or of steel for a steel nail.

However, the component may also consist of a biocompatible plastic, such as polyethylene, especially of a high molecular weight polyethylene (HMWPE). The advantage of these materials lies therein that, on the one hand, they are not too hard and, on the other, there is no breakdown of the plastic with unknown breakdown products.

The plastic may, however, also be a bioabsorbable polymer, preferably a polylactide. For this embodiment, there is, initially, a clearance-free transverse locking of the medullary nail, which then, with increasing absorption of the polymer, is eliminated successively once again, so that the transverse locking screw becomes movable once again relative to the medullary nail and, with that, also the bone fragments that have been taken care of. Accordingly, after the fracture has been consolidated, there is dynamization of the bone fragments. The fact that the chips, which may be formed when a locking screw is screwed through the transverse borehole of the nail, can be broken down by the body is a further advantage.

The transverse borehole of the nail may be formed either as a circular borehole (a=b) or as an elongated hole (a>b), where a is the maximum dimension of profile F is in the direction of the longitudinal central axis of the nail and b is the maximum dimension perpendicularly thereto.

The locking screw (or a locking bolt), which can be introduced into the transverse borehole, advisably has a shaft with a diameter d with a>d<b. In the case of a locking screw, the diameter d also includes the external thread. The diameter d, moreover, preferably is at least 5% smaller than the smaller of the two dimensions a, b of the cross-sectional profile F.

The component may be mounted or fastened at different places within the medullary nail. Preferably, however, it is fastened to the inner surface of the wall of the medullary nail.

BRIEF DESCRIPTION OF THE DRAWINGS

The invention and further developments of the invention are explained in even greater detail in the following by means of the partially diagrammatic representation of several examples in the drawings, in which:

FIG. 3 shows a longitudinal section through a variation of the medullary nail;

FIG. 4 shows a longitudinal section through a further variation of the medullary nail; and FIG. 5 shows a section through the medullary nail along the line V-V of FIG. 4.

DETAILED DESCRIPTION OF THE PREFERRED EMBODIMENTS

Figure 1:
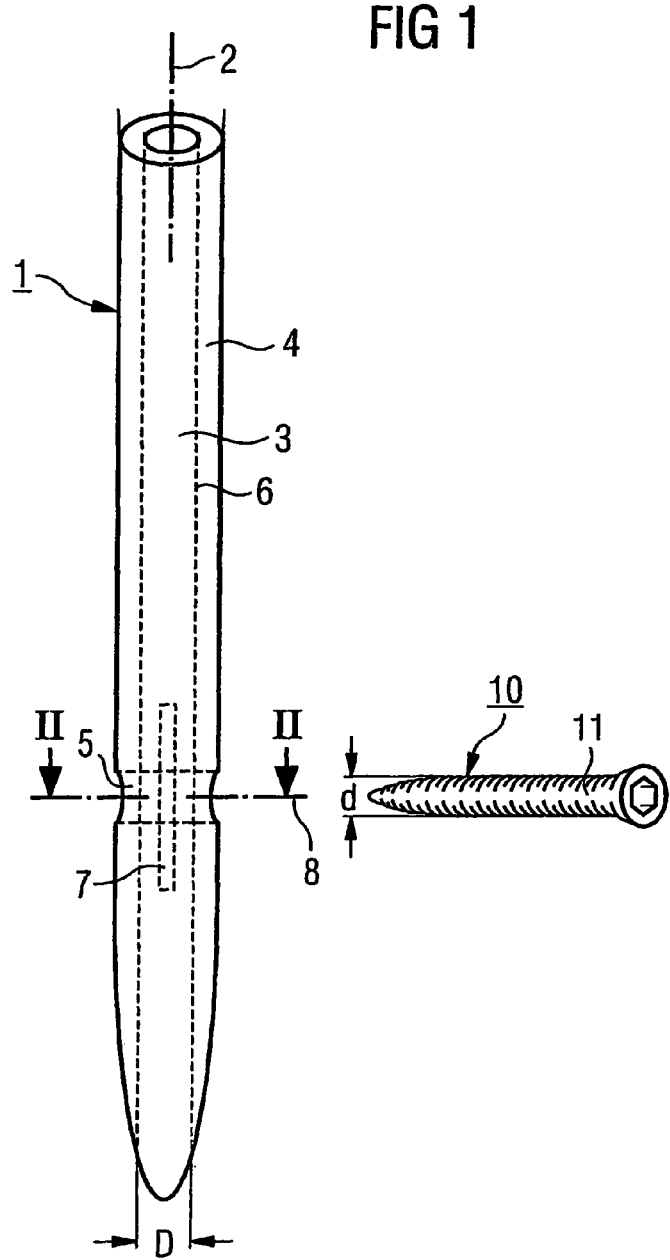
FIG. 1 shows a perspective view of the inventive medullary nail.
Figure 2:
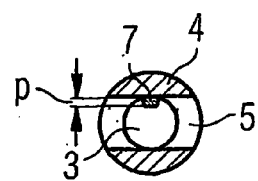
FIG. 2 shows a section through the medullary nail along the line II-II of FIG. 1.

The surgical nail 1, shown in FIGS. 1 and 2, is an intramedullary nail for tubular bones with a central axis 2 and consists of a metal or metal alloy, that is, of a material with a relatively high strength. Moreover, the surgical nail 1 has a transverse borehole 5, which extends transversely to the central axis 2, has a cross-sectional profile F and a transverse axis 8. The transverse borehole 5 is produced proximally and constructed as a circular borehole. However, it could also be constructed as an elongated hole with the maximum dimensions a and b, the longer dimensioned a being disposed in the axial direction.

The medullary nail has a longitudinal borehole 3, which extends coaxially with the central axis 2 and, as a result, a casing 4 with the inner surface 6. In the longitudinal borehole 3 in the region of the transverse borehole 5, a component 7, narrowing the cross-sectional profile F of the transverse borehole 5, is fastened to the inner surface 6 of the casing 4. In the example shown, the component 7 is mounted in the rear region of the longitudinal borehole 3 and has a protruding thickness P. The thickness P is selected so that the locking screw 10 with the external thread 11 can barely still be screwed into the transverse borehole 5, e.g., P>0.01 D, and, preferably, P>0.05 D protruding radially into the longitudinal borehole.

The component 7 consists of a pin or stud, which is aligned essentially parallel to the longitudinal axis 2. Instead of a stud, a different longitudinal component may also be used, such as a piece of wire, a piece of cable or a profiled piece.

In FIG. 3, a variation of the inventive medullary nail is shown, for which the component 7 is constructed as a separate element, which can be introduced by means of a suitable instrument 20 intraoperatively into the longitudinal borehole 3 of the medullary nail 1.

In FIGS. 4 and 5, a further variation of an inventive medullary nail is shown, for which the inner surface 6 of the casing 4 has a groove 9, which extends parallel to the central axis 2 and in which the component 7 can be introduced into the longitudinal borehole 3 starting from the tip 14 of the medullary nail 1. The length of the component 7 is such that, when it is introduced completely into the medullary nail 1, it reaches the region of the transverse borehole 5, so that the cross-sectional profile F is narrowed by the component 7. The groove 9 has a partially circular cross-section with a center angle greater than 180° and, in a preferred embodiment, 200°. The diameter of the component 7, moreover, is such that its part, protruding radially into the longitudinal borehole 6, brings about such a narrowing of the cross-sectional profile F, that passage of the locking bolt 12 with the smooth shaft 13 is barely still possible.

While the present invention has been described with reference to the preferred embodiments, those skilled in the art will recognize that numerous variations and modifications may be made without departing from the scope of the present invention. Accordingly, it should be clearly understood that the embodiments of the invention described above are not intended as limitations on the scope of the invention, which is defined only by the following claims.

What is claimed:

1. An intramedullary nail comprising:
a nail body having a central longitudinal axis, an outer wall surrounding a longitudinal bore and defining an inner wall surface, and a transverse opening through the outer wall, the transverse opening having a central axis and a cross-sectional profile F and configured for receiving a bone fixation element;
a longitudinal component disposed within the longitudinal bore and extending partially into the transverse opening to abut against a bone fixation element inserted through the transverse opening without being penetrated by the bone fixation element; and wherein the inner wall surface of the nail includes a longitudinal groove having a partially circular cross section that extends parallel to the central axis, the groove is configured and dimensioned for receiving the component.

2. The device of claim 1, wherein the component is integrally attached to the inner wall surface of the nail body.

3. The device of claim 1, wherein the component is selected from the group consisting of a pin, a stud, a cable, section of wire.

4. The device of claim 1, wherein the component is aligned parallel to the central longitudinal axis of the nail.

5. The device of claim 4, wherein the portion of the component that contacts the bone fixation element when inserted through the transverse opening is aligned parallel to the central longitudinal axis.

6. The device of claim 1, wherein the nail and the component are formed of the same material.

7. The device of claim 1, wherein the component is formed of polyethylene, a high-molecular weight polyethylene (HMWPE) or other biocompatible plastic.

8. The device of claim 1, wherein the component is formed of a bioabsorbable polymer or copolymer.

9. The device of claim 1, wherein the cross-sectional profile F of the transverse opening has a maximum length a in the direction of the longitudinal central axis of the nail and a maximum width b perpendicularly thereto, where a>b.

10. The device of claim 9, wherein the bone fixation element nail is a bone screw with an external thread having a maximum diameter d, where a>d<b.

11. The device of claim 10, wherein the diameter d is at least 5% smaller than the smaller of the two dimensions a, b.

12. The device of claim 1, wherein the component is a separate element configured for introduction into the longitudinal bore of the nail at the time of a surgical procedure.

13. The device of claim 1, wherein the partially circular groove defines a central angle greater than 180 degree.

14. The device of claim 1, wherein the longitudinal bore of the nail has a diameter D, and the component has a maximum thickness of P>0.01 D protruding radially into the longitudinal bore.

15. The device of claim 14, wherein the component has a maximum thickness of P>0.05 D protruding radially into the longitudinal borehole.

16. An intramedullary nail comprising:
a nail body having a central longitudinal axis, an outer wall surrounding a longitudinal bore and defining an inner wall surface, wherein the inner wall surface of the nail includes a longitudinal groove having a partially circular cross section that extends parallel to the central axis, the groove is configured and dimensioned for receiving a component, and a transverse opening through the outer wall, the transverse opening having a central axis and a cross-sectional profile F and configured for receiving a bone fixation element; and a longitudinal component aligned parallel to the longitudinal central axis of the nail and configured and dimensioned for insertion into the longitudinal groove such that the longitudinal component extends partially into the transverse opening to abut against a bone fixation element inserted through the transverse opening without being penetrated by the bone fixation element.

17. A method for repairing bone fractures comprising:

providing an intramedullary nail for insertion into the medullary canal of a fractured bone, the intramedullary nail having a nail body with a central longitudinal axis, an outer wall surrounding a longitudinal bore, an inner wall surface, and a transverse opening through the outer wall, where the transverse opening has a cross-sectional profile F and is configured for receiving a bone fixation element and wherein the inner wall surface of the nail includes a longitudinal groove having a partially circular cross section that extends parallel to the central axis, the groove is configured and dimensioned for receiving a component;

inserting a longitudinal component within the longitudinal bore of the nail such that the longitudinal component extends partially into the transverse opening;

inserting at least one bone fixation element through the transverse opening in the intramedullary nail such that the bone fixation element abuts the longitudinal component without penetrating the longitudinal component.

* * * * *